United States Patent [19]
Purdy

[11] B 3,981,750
[45] Sept. 21, 1976

[54] ELECTRICAL GENERATOR

[75] Inventor: David L. Purdy, Indiana, Pa.

[73] Assignee: Coratomic Inc., Indiana, Pa.

[22] Filed: July 12, 1973

[21] Appl. No.: 378,513

[44] Published under the second Trial Voluntary Protest Program on January 27, 1976 as document No. B 378,513.

[52] U.S. Cl. .............................. 136/202; 250/206
[51] Int. Cl.² ........................................ G21H 1/10
[58] Field of Search ........... 136/202, 205, 208, 232; 250/506

[56] References Cited
UNITED STATES PATENTS

| | | | |
|---|---|---|---|
| 3,076,051 | 1/1963 | Haba | 136/201 X |
| 3,262,820 | 7/1966 | Whitelaw | 136/202 |
| 3,481,794 | 12/1969 | Kasschau | 136/208 |
| 3,533,913 | 10/1970 | Botts et al. | 136/202 UX |
| 3,607,443 | 9/1971 | Purdy | 136/202 |
| 3,663,306 | 5/1972 | Des Champs et al. | 136/202 |
| 3,668,015 | 6/1972 | Streb et al. | 136/202 |
| 3,697,329 | 10/1972 | Bunker et al. | 136/202 |
| 3,758,346 | 9/1973 | Falkenberg et al. | 136/202 |
| 3,818,304 | 6/1974 | Hursen et al. | 136/202 |

OTHER PUBLICATIONS

Transactions of A.N.S., Vol. 13, No. 2, Nov. 13, 1970, (pp. 504, 505), Article Entitled, *A Radioisotope Fueled Vapor Cycle Power Supply For An Artificial Heart* by Huffman et al.

*Primary Examiner*—Verlin R. Pendegrass
*Attorney, Agent, or Firm*—Hymen Diamond

[57] ABSTRACT

A nuclear heart pacer having a heat-to-electricity converter including a solid-state thermoelectric unit embedded in rubber which is compressed to impress hydrostatic precompression on the unit. The converter and the radioactive heat source are enclosed in a container which includes the electrical circuit components for producing and controlling the pulses; the converter and components being embedded in rubber. The portions of the rubber in the converter and in the container through which heat flows between the radioactive primary source and the hot junction and between the cold junction and the wall of the container are of thermally conducting silicone rubber.

The primary radioactive source material $Pu_{238}$ is encapsuled in a refractory casing of WC-222 (T-222) which in turn is encapsuled in a corrosion-resistant casing of platinum rhodium, a diffusion barrier separating the WC-222 and the Pt-Rh casings. The Pt-Rh casing is in a closed basket of tantalum. The tantalum protects the Pt-Rh from reacting with other materials during cremation of the host, if any. The casings and basket suppress the transmission of hard X-rays generated by the alpha particles from the $Pu_{238}$. The outside casing of the pacer is typically of titanium but its surface is covered by an electrically insulating coating, typically EPOXY resin, except over a relatively limited area for effective electrical grounding to the body of the host. It is contemplated that the pacer will be inserted in the host with the exposed titanium engaging a non-muscular region of the body.

22 Claims, 13 Drawing Figures

COLD SIDE

FIG. 10.

HOT SIDE

ELECTRICAL GENERATOR

BACKGROUND OF THE INVENTION

This invention relates to the generation of electricity by thermoelectric conversion of heat from a local primary source and has particular relationship to nuclear heart pacers or pacemakers. To the extent that this invention has other uses than in heart pacers it is understood that such uses are within the scope of this application.

A nuclear heart pacer includes a primary source of radioactive material, a thermoelectric converter which converts the heat from the source into electricity, and an electrical circuit powered by the converter which converts the output of the thermoelectric converter into pulsations and controls the flow of the pulsations to the heart. The primary source is typically composed of plutonium 238 which emits alpha particles. Such particles have a short range but in passing through material the alpha particles produce X-rays which have a long range. The quantity of radioactive material which is used is usually sufficient to produce the power necessary for the pacer over a period of about 20 years. In accordance with the teachings of the prior art this quantity is between one-third and one-half gram of $Pu_{238}$. It is desirable that this quantity of radioactive material be minimized both to minimize the hard X-rays and also because the cost of $Pu_{238}$ is very high and at the same time to increase the useful life of the pacer and this is an object of this invention.

In accordance with the teachings of the prior art the thermoelectric converter is a thermopile formed of wires. It has been realized, in arriving at this invention, that the quantity of radioactive material may be reduced by replacing the wire thermopile with a thermoelectric unit of the solid-state type. However, in the use of the prior-art nuclear heart pacers, it was discovered that the normal physical activities of the person or animal, having a heart pacer, subject the pacer to relatively high mechanical shocks or impacts which damage the pacer. Solid-state thermoelectric elements are brittle and fragile and substantially incapable of withstanding tensile stress and a heart pacer having a solid-state thermoelectric unit may in a short time after installation be damaged as a result of the normal physical activities of the host.

It is an object of this invention to overcome these disadvantages and to provide a heart pacer having a solid-state thermoelectric unit in which the converter and other related components shall be protected from physical or mechanical shocks and impacts resulting from the normal activities of the host.

SUMMARY OF THE INVENTION

In accordance with this invention a heart pacer is provided including a solid-state thermoelectric unit which is embedded or potted in a medium capable of applying hydrostatic stress. The medium is compressed hydrostatically subjecting the thermoelectric unit to hydrostatic precompression. When the pacer is subjected to physical shock, the precompression counteracts the stress impressed by the shock and the thermoelectric unit is not damaged. In addition, the thermoelectric converter, the primary source and the components of the electrical circuit for converting the output of the thermoelectric converter into pulses are potted or embedded in an outer container, in the same medium. The portions of the embedding medium between the hot junction and the primary source and between the cold junction and the container, which serves as heat sink, are highly thermally conducting to facilitate the necessary heat flow between the junctions of the thermoelectric converter and the source and sink. It is to be understood that while the embedding and the precompression has unique advantages in apparatus in which the thermoelectric unit is of the solid-state type, it has more general advantages for thermoelectric units of other types and to the extent that this concept is used, as taught in this application, with such other thermoelectric units, such use is within the scope of this invention.

The primary source is a radioactive block enclosed in a high-strength capsule, typically of WC-222 alloy. The highstrength capsule is enclosed in a corrosion-resistant capsule, typically of platinum rhodium. A diffusion barrier, typically of aluminum oxide, is interposed between these capsules. This encapsulated unit is contained in a closed basket, typically of tantalum.

BRIEF DESCRIPTION OF THE DRAWINGS

For a better understanding of this invention, both as to its organization and as to its method of operation, together with additional objects and advantages thereof, reference is made to the following description, taken in connection with the accompanying drawings, in which.

DETAILED DESCRIPTION OF EMBODIMENT

Figure 1:
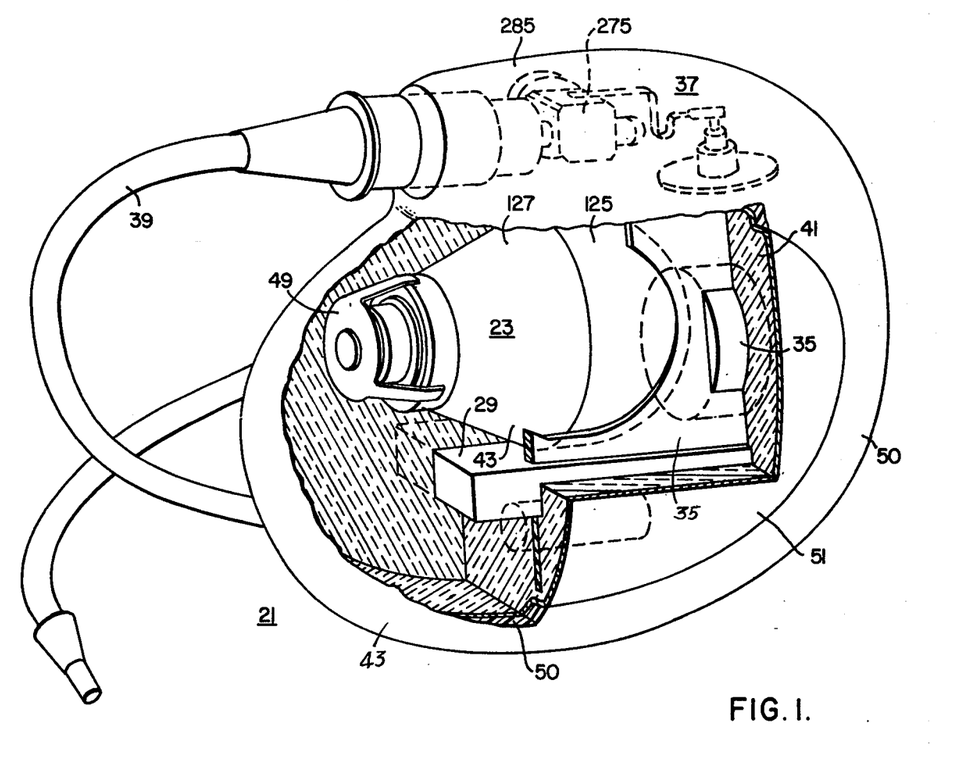
FIG. 1 is a view in perspective of a heart pacer in accordance with this invention with parts of the outer container broken away to show the interior.
Figure 2:
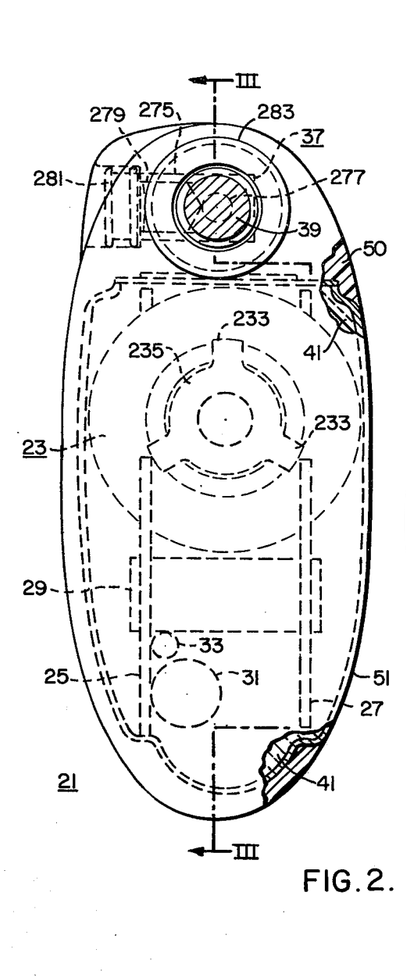
FIG. 2 is a view in end elevation with parts sectioned of the heart pacer shown in FIG. 1.
Figure 3:
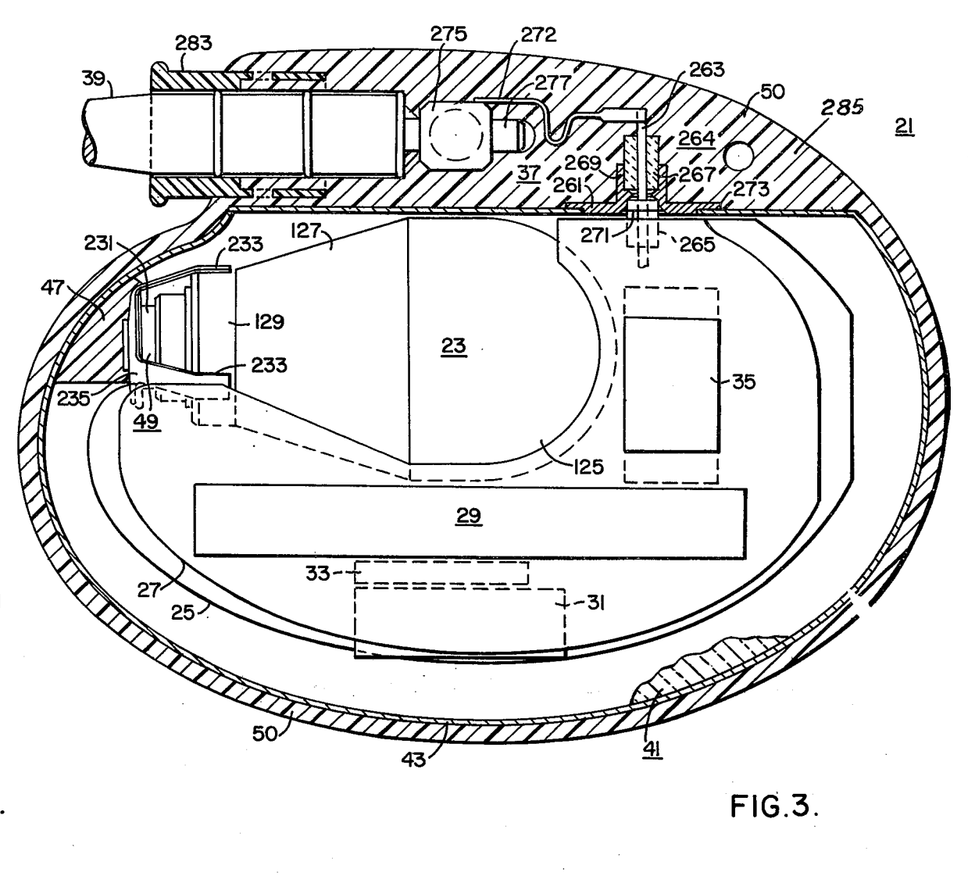
FIG. 3 is a view in section taken along lines III—III of FIG. 2.

The apparatus shown in the drawings is a heart pacer 21 (FIGS. 1–3) including a battery 23, printed circuit boards 25 and 27 (FIG. 2), a solid-state electronics package 29, a storage capacitor 31, a magnetic switch 33, a transformer 35 and an output assembly 37 for connecting the output of the transformer 35 to the catheter or heart lead 39 which is placed on the heart muscle. The boards 25 and 27 serve as a cradle for the battery 23. The battery 23 and the circuit components 25–35 are embedded in a potting compound 41 (FIG. 1) of a resilient material in a container 43 typically of an alloy predominantly of titanium. The potting compound 41 is typically predominately 2CN, a silicone rubber which is thermally insulating and which responds to pressure like a fluid, transmitting pressure uniformly in all directions. The 2CN is sold by Emerson-Cummings Corp. of Pittsburgh, Pa. However, a portion 47 (FIG. 3) of the compound between the cold-junction end 49 of the battery 23 and the container 43 is composed of a thermally highly-conducting material, typically ECCOSIL 4952, a silicone rubber. ECCOSIL 4952 is sold by Microtechtronics Corp., Buffalo, N.Y. The container 43 is encased in window coating 50 of EPOXY resin except for a winder 51 (FIG. 2). The container 43 serves as ground for the electrical circuit 25–35 and as a radio-frequency shield for the pacer and the window 51 serves to connect the ground to the body of the host. The window 51 projects outwardly from the remainder of the container 43 and is flush with the EPOXY coating 50 as shown in FIG. 2. Typically, the heart pacer 21 has an overall length of 2.45 inches, a width of 1.88 inches and a depth of 0.80 inch. Typically, the window or dimple 51 has a heighth of about 0.050 inch and is of oval shape about 1.8 inches by 1.1 inches.

The battery 23 (FIG. 4) includes a primary source 61 and a solid-state thermoelectric converter 63. The source 61 is enclosed in a highly evacuated container 65 encompassed by a heat shield 67.

Figure 4:
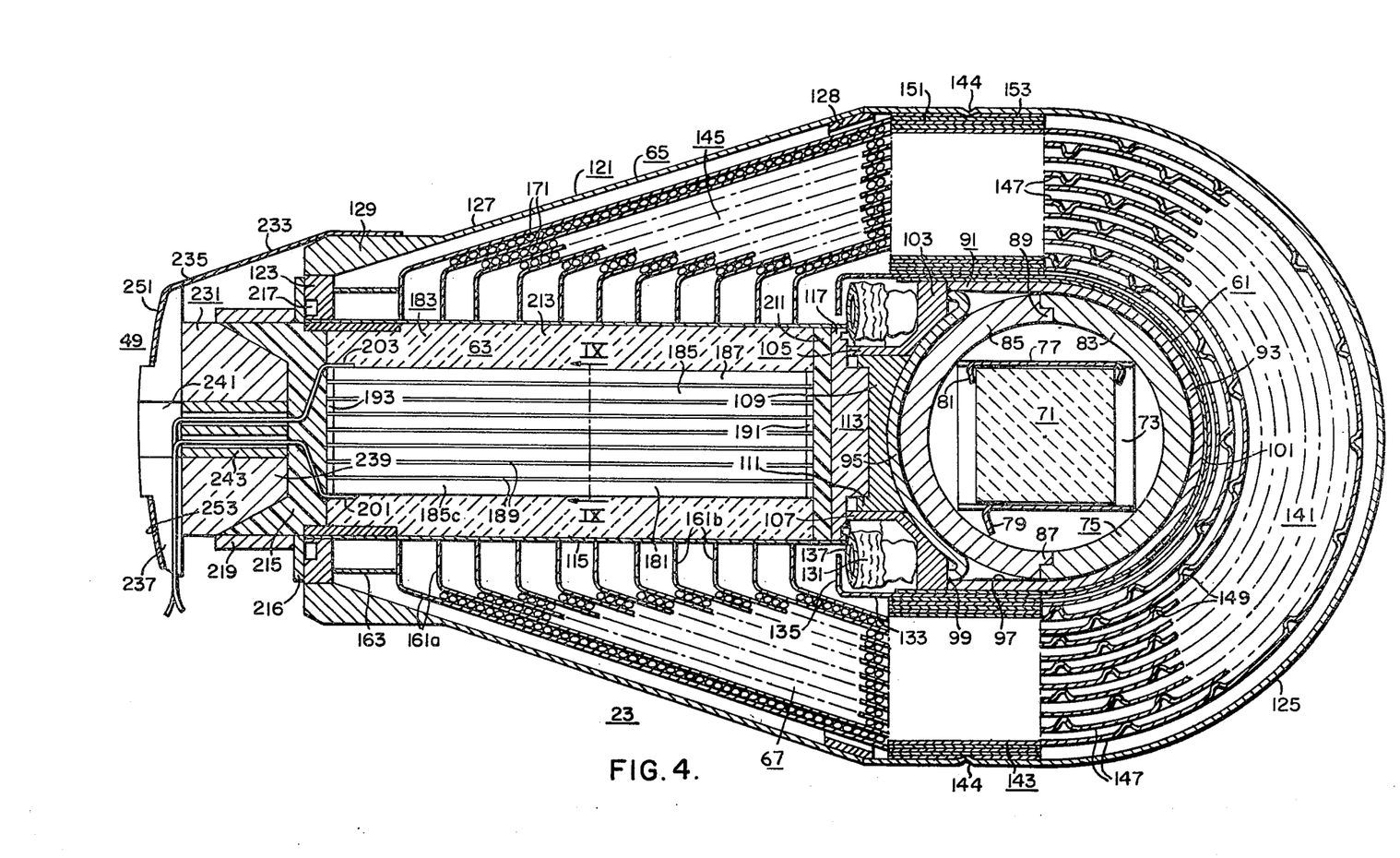
FIG. 4 is a view in longitudinal section of the battery of the heart pacer shown in FIGS. 1–3.
Figure 6:
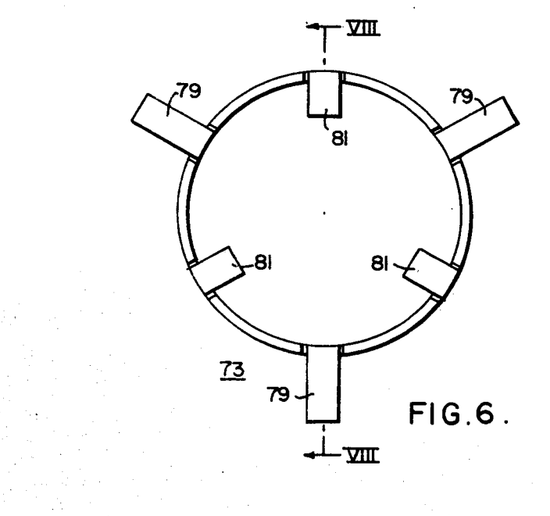
FIG. 6 is a view in end elevation of the cylindrical bracket for positioning the radioactive block of the capsule shown in FIG. 4 as viewed from one end.
Figure 7:
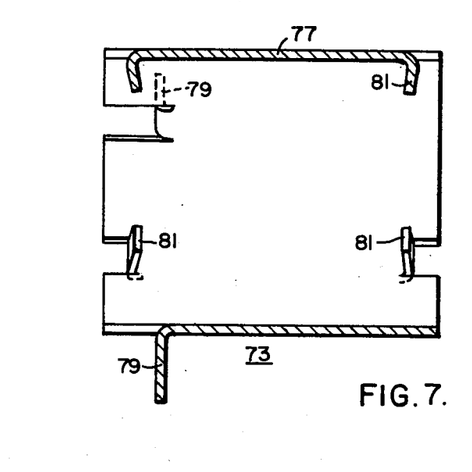
FIG. 7 is a view in end elevation of this bracket as viewed from the opposite end.
Figure 8:
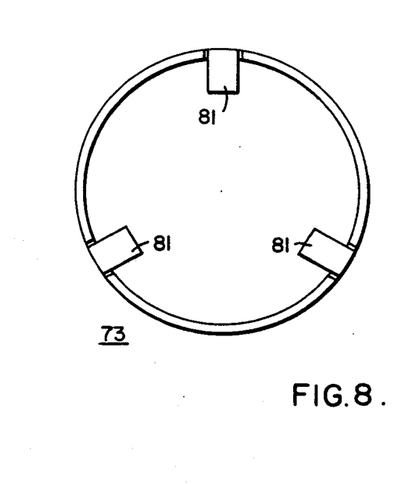
FIG. 8 is a view in section taken along line VIII—VIII of FIG. 7.

The source 61 includes a ceramic block 71 formed of a powder of plutonium-oxide, the plutonium being predominately $Pu_{238}$. Typically, this source includes about 0.272 gram of $Pu_{238}O_2$. This fuel is sufficient to operate the pacer according to this invention for 20 years without renewal of the source. The source delivers 117 milliwatts initially and 100 milliwatts at end of 20 years. The block 71 is mounted in positioning bracket 73 in inner capsule 75, a hollow sphere. The bracket 73 (FIGS. 6, 7, 8,) is formed of a hollow cylinder 77 having tabs 79, spaced about 120°, projecting outwardly from one end and tabs 81, interposed between tabs 79 and spaced about 120°, and projecting inwardly from both ends. The block 71 is supported within the bracket 73 by the tabs 81. The spacing between the tabs 81 is set to accommodate the length of the block 71 between the tabs 81. Typically, tabs 81 at one end are first projected inwardly; the block 71 is then inserted in cylinder 77 engaging tabs 81; thereafter, tabs 81 at the other end are bent to engage and hold the block 71. The tabs 79 engage the inner surface of sphere 75 and help to secure the bracket 73 in the sphere 75. Tabs 79 are bent inwardly from the 90° position about 15° as shown in FIG. 4.

The inner capsule 75 is formed of hollow hemispheres 83 and 85, the rims of the hemispheres being provided with cooperative projections 87 and 89 respectively which are coextensively engaged to form the sphere 75. The hemispheres 83 and 85 are closely dimensioned to about 0.001 inch. Typically, the sphere is composed of a tantalum alloy, WC-222, has an inside radius of 0.125 inch and an outside radius of 0.155 inch. WC-222 has the following chemical composition: W 9.6—11.2 percent, HF 2.2–2.8 percent, C 0.008–0.0175 percent, Ta balance. The bracket 73 typically has a length of about .186 inch and a diameter of about 0.125 inch. The inner capsule 75 is fire resistant and has high strength so that the block 77 remains locked in the inner capsule regardless of what impacts the heart pacer may suffer and also if the host should be cremated. The tantalum alloy also absorbs hard X-rays.

The inner capsule 75 is enclosed in an outer capsule 91 including a hood 93 formed of a hemisphere from which a cylinder extends; a spherical dish-shaped member 95 is sealed to the rim of the cylinder. Typically, the hemisphere and cylinder of the hood 93 have an inner diameter of 0.316 inch and a thickness of about 0.010 inch. The member 95 has the same thickness and is correspondingly dimensioned to seal to the hood 93. The outer capsule 91 is composed of platinum-rhodium alloy $Pt_{10}Rh$. The outer capsule 91 protects the source 61 against corrosion and oxidation. A diffusion barrier 97, aluminum oxide, typically of about 0.001 inch thickness, is disposed between the inner capsule 75 and the outer capsule 91. This barrier prevents the alloying of the inner and outer capsules 75 and 91. During assembly the block 71 is secured in the bracket 73 with the tabs 81 holding the block. The bracket 73 and block 71 are then inserted between the hemispheres 83, 85 and the hemispheres are joined at the steps 87 and 89 into a sphere. The sphere is then welded in an inert-gas (argon) atmosphere. The sphere 75 is then inserted between the members 93 and 95 of the outer capsule 91 and this capsule is welded at the joint 99 between these members.

The unit 71-75-91 is disposed in a basket 101 typically of tantalum. The basket 101 is in the form of a hollow hemisphere terminating at its rim in a hollow cylinder. Typically, the basket 101 is about 0.005 inch in thickness. Near its outward end the basket 101 is welded to the flange 103 of a flanged sleeve 105, typically of tantalum. The stem 107 of the sleeve 105 merges into the flange 103, at their inner surfaces, the transition surface being a spherical annular surface of the same radius as the dish-shaped member 95. The dish-shaped member 95 is seated in this surface. The stem 107 is welded to a disc 109, typically of tantalum. The inner surface of the disc 109 is spherical and coextensive with the spherical annular surface of the flange 105 and of the same radius and the member 95 is seated in this surface. The disc 109 has an outwardly projecting rim 111.

A flanged disc 113 is brazed to the rim 111. This disc 113 is composed of the titanium alloy Ti6A14V. A cylinder 115, also typically of Ti6A14V, which contains the converter 63 is welded to the flange 117 of the disc 113. The flange 117 is trepanned to limit the flow of heat from the weld. The alloy Ti6A14V has high strength and low thermal conductivity and is used for this reason.

The evacuated container 65 is defined by outer shell 121 and the cylinder 115. These members 115 and 121 are joined by a ring 123 typically of Ti6A14V. The shell 121 is typically composed of titanium and includes a hollow hemispherical end 125 from the rim of which a cylinder extends. A hollow frusto-conical shell 127 extends from the rim of the cylinder. The cylindrical rim of the end 125 and the shell 127 are joined by a weld. A backing annulus, typically of titanium, 128 is provided behind the welded joint. The end 125 and the shell 127, throughout the major portion of its length, have a thickness typically of 0.010 inch. But the shell 127 flares out at its constricted end 129, to a thickness of about 0.090 inch. The thickened end 129 is chamfered on the outside and flattened on the inside and is welded to the ring 123 around the flattened area. The ring 123 is internally welded to the cylinder 115. A reinforcing ring 124 internally of the cylinder 115 forms a part of the welded joint between the cylinder 115 and the ring 123. The ring is trepanned to suppress the flow of heat from the weld.

The vacuum within container 65 is maintained by a getter 131 typically CERRALOY 400. The getter 131 is mounted in an annular space provided between the sleeve 107, the flange 103, and a cylinder 133 which extends from the rim of the basket 101 and is bent inwardly at teeth 135 extending from its end. The getter 131 is held by a ring 137, typically of var-glass tubing.

The heat shield 67 has a hemispherical section 141, a cylindrical section 143 and a conical section 145. The hemispherical section 141 includes a plurality of hemispheres 147, typically of MONEL metal, concentric with ring 75 and extending between the spherical part of the basket 101 and the inner surface of the end 125. The hemispheres have dimples 149 so that their spacing is maintained. The cylindrical section 143 includes a tape of alternate layers of MONEL metal foil 151, typically .125 inch wide by 0.001 inch thick, and "E" glass insulation 153, typically, 0.125 inch wide by 0.005 inch thick. The tape is wrapped about a center formed of the cylindrical parts of the hood 93 of the outer capsule 91 and the basket 101 and the strip 133 which holds the getter 131. The cylindrical section 143 firmly engages the basket 101 and strip 133 and supports the assembbly 71-75-91, which is relatively heavy, radially and prevents its displacement radially. Radial displacement of the assembly 71-75-91 exerts a torque on the joint 115-123-124 and may rupture this joint. So that the section 143 firmly engages the assembly 71-75-91, dimples 144 are provided in shell 125. The conical section 145 includes a plurality of hollow frusto-conical shells 161 coaxial with the cylinder 115, typically composed of MONEL metal, each extending from the cylindrical shield 143 to a position above the ring 123. The shells 161 are bent over perpendicularly to the cylinder 115 near the ring 123 and are positioned by an annular spacer 163, typically of Ti6A14V.

The head 125 and the conical section 127 are initially separate pieces with the backing ring 128 tack-welded to the hemispherical head 125. In assembling the container 121 the ring 123 is welded to the end 129 of the conical section 127 of the container 65. The strip (typically 0.005 inch thick) which forms the holder 133 for the getter 131 is wrapped around the cylindrical end of the basket 101. The getter 131 and the glass tubing 137 are inserted and the teeth 135 of the strip are bent so as to hold the getter 131 and the tubing. The tape 151-153 is wrapped around the center 133-101-93. The hemispherical shells 147 are positioned about the hemispherical portion of the basket 101 and the head 125 is positioned over the outermost shell 147. The rims of the shells 147 engage the cylindrical shield 143. The frusto-conical shells 161 are stacked in the frusto-conical section 127 between the spacer 163 and the end of the section 127. Several of the larger shells 161a are of 0.005 inch thickness titanium; the other shells 161b are of 0.004 inch thick MONEL. A tube 171 of E-glass insulation is wound about each shell 161 supporting the adjacent shell. The sections 125 and 127 are then abutted with backing ring 128 extending between the rims of these members (125, 127). The assembly is then placed in a chamber which is evacuated to a pressure of $10^{-6}$ Torr and the joint between the rims of the members 125 and 127 is welded and treated out so that the low pressure is maintained.

The thermoelectric converter 63 is disposed in cylinder 115 and includes a solid-state thermoelectric unit 181 embedded or potted in a medium 183 which responds to compression like a fluid, hydrostatically, transmitting the compression in all directions.

Figure 9:
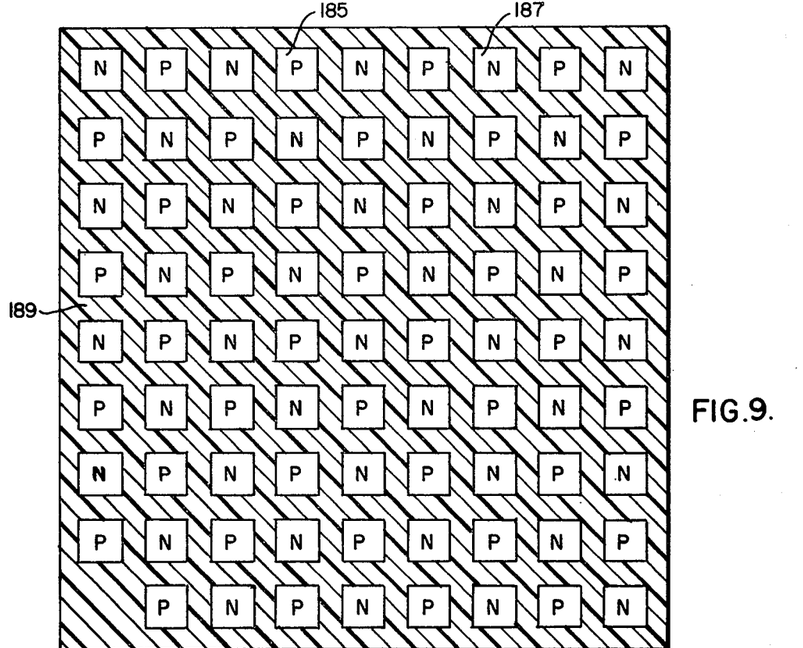
FIG. 9 is a view in section taken along line IX—IX of the portion of FIG. 4 showing the thermoelectric unit.
Figure 10:
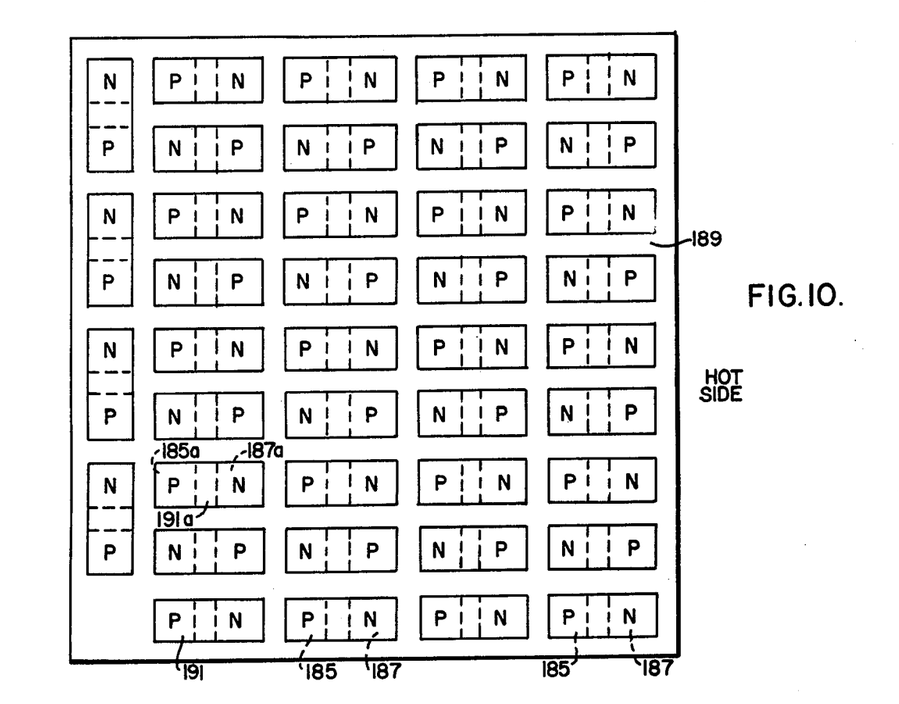
FIG. 10 is a view in end elevation of the thermoelectric unit as viewed from the hot-junction end.
Figure 11:
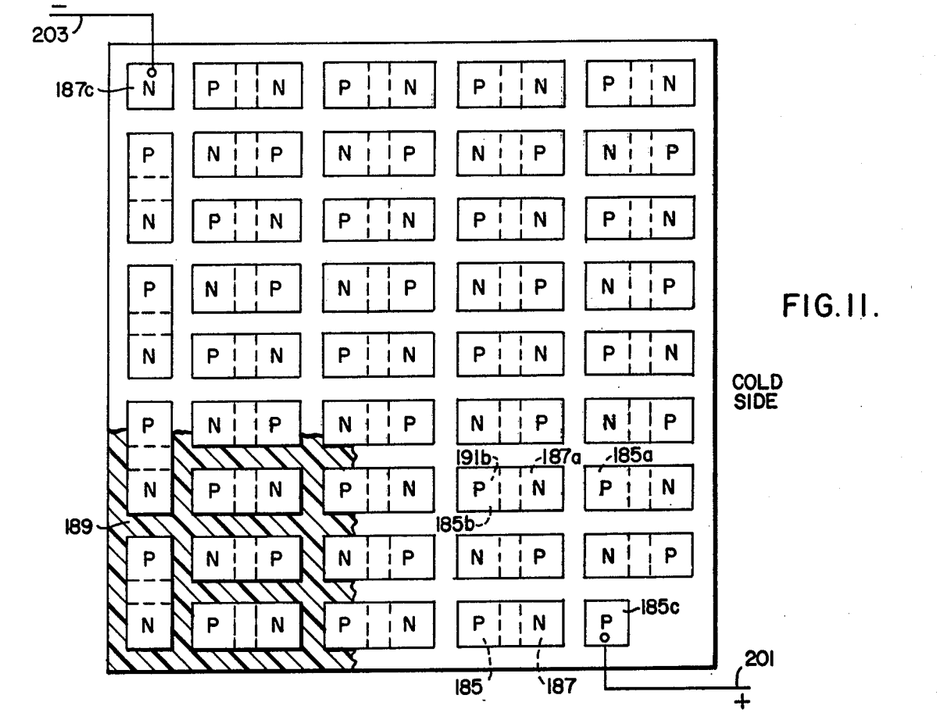
FIG. 11 is a view in end elevation of the thermoelectric unit as viewed from the cold-junction end.
Figure 12:
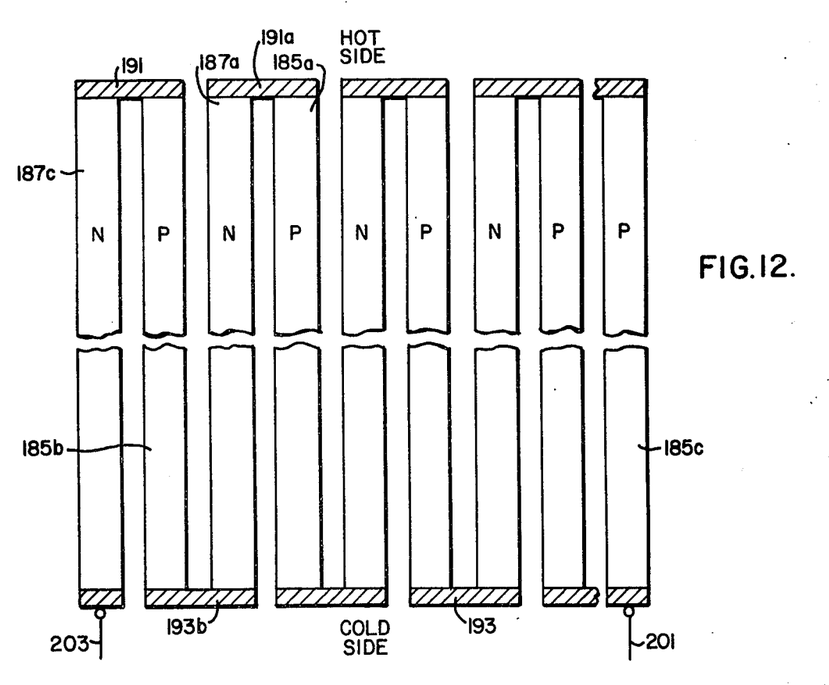
FIG. 12 is a diagrammatic view showing the manner in which the individual thermoelectric elements of the thermoelectric unit are interconnected.

The thermoelectric unit 181 includes a plurality of positively and negatively doped strips 185 and 187, typically of bismuth telluride, embedded in polymeric insulation 189 (FIG. 9) such as EPOXY. So embedded the block is itself stress resistant and protects the strips 185 and 187 from rupture. Typically, there may be eight-one of such strips 185 and 187 arrayed as shown in FIG. 9. Successive negative and positive strips are interconnected by solder strips 191 (FIG. 12) at the hot-junction of the unit 181 and alternate pairs of positive and negative strips are interconnected by solder strips 193 (FIG. 12) at the cold-junction. Typically, positive strip 185a and negative strip 187a are interconnected by solder strip 191a at the hot-junction (FIG. 12) and negative strip 187a and positive strip 185b are interconnected by solder strip 193b at the cold-junction. Diagonally positioned positive and negative end strips 185c and 187c (FIG. 11) are connected to output conductors 201 and 203. The pairs of strips 185 and 187 of the array of strips form thermocouples connected in series between conductor 201 and conductor 203.

The potting 183 (FIG. 4) includes a disc 211 of thermally conducting resilient material, typically silicone rubber ECCOSIL 4952, interposed between the source 61 and the thermoelectric unit 181, a hollow cylinder 213 of thermally insulating material, typically rubber, SYLGARD 184, encircling the unit 181, and a disc 215 of ECCOSIL 4952 having an internally generally frustoconical rearward projection. SYLGARD 184 is sold by Techtronic Corporation of Buffalo, N.Y. The potting material 211-213-215 serves as axial support for the cylinder 115 and prevents the assembly 41-75-91-141-143 from buckling the cylinder 115.

The converter 63 is assembled in the cylinder 115. First, the cylinder 211 is deposited on the trepanned disc 109. Next, the thermoelectric unit 181 is positioned centrally on the disc 211. Then the cylinder 213 is deposited around the unit 181. A washer, 216, typically of titanium is then positioned to cover the trepan groove 217 of the disc 123. A split ring 219, typically of Ti6A14V alloy, is placed coaxially with the cylinder 115 on the washer 216. The ring 219 is resilient but has a high restoring force. A cylindrical mass of thermally conducting material, typically ECCOSIL 4952, is then deposited in the cylindrical space defined by the ring 219, the washer 216 and the disc 123. Before this mass is cured a plug 231 is positioned at the outer edge of the mass.

The plug 231 is typically composed of electrolytic grade copper and has a head 237 split at the center and a body 239 which terminates in a generally frusto-conical portion. The body 237 has a central opening which communicates with an opening 241 in the head. This opening has a bushing 243.

Figure 5:
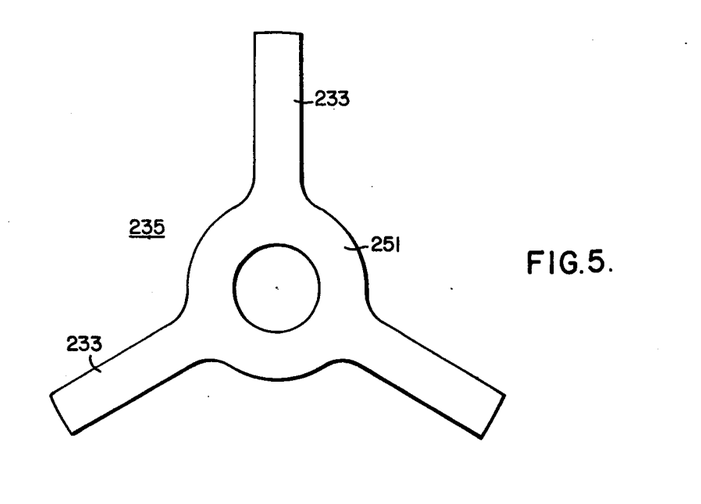
FIG. 5 is a plan view of the strap assembly which applies pressure to compress the medium in which the thermoelectric unit is embedded.

The conductors 201 and 203 are brought out centrally before the cylindrical mass is deposited within the inner ring 219, the washer 216 and the disc 123. After the mass is deposited, but before it cures, the conductors 201 and 203 are strung through the ceramic bushing 243 of the plug 231 and brought out through the slot between the parts of the head 237. The plug 231 is then set at the outer end of the mass 231 of thermally conducting material, while being maintained coaxial with the cylinder 115. As the mass is cured the ring 219 prevent the mass from expanding radially. Once the mass is cured the plug 231 is pressed into the mass building up hydrostatic pressure within the potting material 183. The split ring 219 confines the mass radially but the gap in this spring opens to a predetermined spacing which measures the compression of the mass. The force exerted on the mass of ECCOSIL 4952 may be as high as 150 pounds; however, where the thermoelectric unit 181 is stress resistant, the force may be as low as 15 pounds. When the gap in the ring has the desired spacing the mass is secured by straps 233 of spring 235. The spring 235 (FIG. 5) is composed of sheet titanium alloy, typically about 0.005 inch in thickness. This spring has an annular center 251 from which the straps 233 extend radially uniformly spaced around its periphery. In securing the plug 241, the center 251 is spot welded to the sloping shoulder 253 of the head and the straps 233 are bent around the head and spot welded to the thickened portion 129 of the shell 127.

Initially the container 43 (FIGS. 1, 2, 3) which is composed of commercially pure titanium is in two parts. One part has an opening 261 for the output conductor 263 from the transformer 35. Initially the batter 23, the printed circuit boards 25 and 27, block 29, containing the circuit components (integrated circuit and separate transistors not shown) potted in EPOXY resin, the storage capacitor 31, the magnetic switch 33 and the transformer 35 are assembled and connected outside of the container 43.

The output conductor 263 is also initially connected into a feed-through assembly 264. This assembly includes a ferrite radio-frequency filter 265 which suppresses electromagnetic disturbances and which encircles the conductor 263. The assembly also includes a ceramic insulating sleeve 267 through which the conductor 263 is sealed gas-tight. The sleeve 267 is sealed into a flanged sleeve 269, typically of titanium. The ferrite filter 265 is secured to the inner side of the flanged sleeve 269 by a spring washer 271. The conductor 263 is connected near its external end to a flexible connector 272.

Once the components are interconnected the battery 23 and the parts 25–35 are mounted in one of the parts of the container 43 with the battery cradled between the boards 25 and 27. The boards 25 and 27 are contoured to rest on the inner surface of the container 43. The ground conductors (FIG. 13) are connected to the container 43. The assembly 264 is disposed adjacent the opening 261 with the flanges 273 of sleeve 269 appropriately positioned adjacent the hole 261. The two parts of the container 43 are then welded to form the container. The ECCOSIL 4952 mass 47 between the cold-junction end 49 of the battery and the container 43 is injected with a syringe inserted through opening 261. The 2CN potting rubber is then injected through opening 261 and encompasses the parts 23 through 35. The container 43 and its content are then placed in a chamber (not shown) which is evacuated and filled with an inert gas (argon) at about one atmospheric pressure. The inert gas permeates the converter 63 through the opening 241 and the bushing 243 (FIG. 4). Within the chamber, in the inert-gas atmosphere, the flange 273 is welded gas-tight to the rim of the hole 261 sealing the hole. The connector 272 is now connected to a terminal block 275.

The terminal block 275 is in the form of a rectangular parallelapiped having a cylindrical opening through which the inner end 277 of the catheter 39 passes. Laterally a set screw 279 (FIG. 2) is provided in the block 275. Over the head of the set screw 279 there is a silastic plug 281.

The catheter 39 is inserted in heart pacer 21 by the doctor who installs it in the host's heart. During the construction of the pacer 21 the catheter 39 is replaced by a pin (not shown) of the diameter of the catheter 39. This pin is encircled by a suture boot 283. The pacer as now assembled is mounted in a mold (not shown) with the dimple 51 which forms the window facing downwardly and masked. The EPOXY resin 50 is then molded about the titanium casing except at the dimple 51 and the EPOXY encapsulation 285 for the conductor 263, the connector 272, the block 275, the boot 283 and the pin (not shown) is formed. The pin is then removed.

After installation in the heart of the host, the catheter 39 is inserted in the opening formed by the pin and the end 277 is secured by the set screw 279 in the terminal block. The head of the set screw is closed by the plug 281 and the plug 281 can be sealed by silastic insulation.

The electrical circuit (FIG. 13) used in the practice of this invention is of the solid-state type and includes, in addition to the magnetic switch 33, a DC to DC converter 301, an amplifier 303, a monostable 305, a noise-rate turn-on 307, a multivibrator reset 309, a multivibrator 311, and an output 313.

Figure 13:
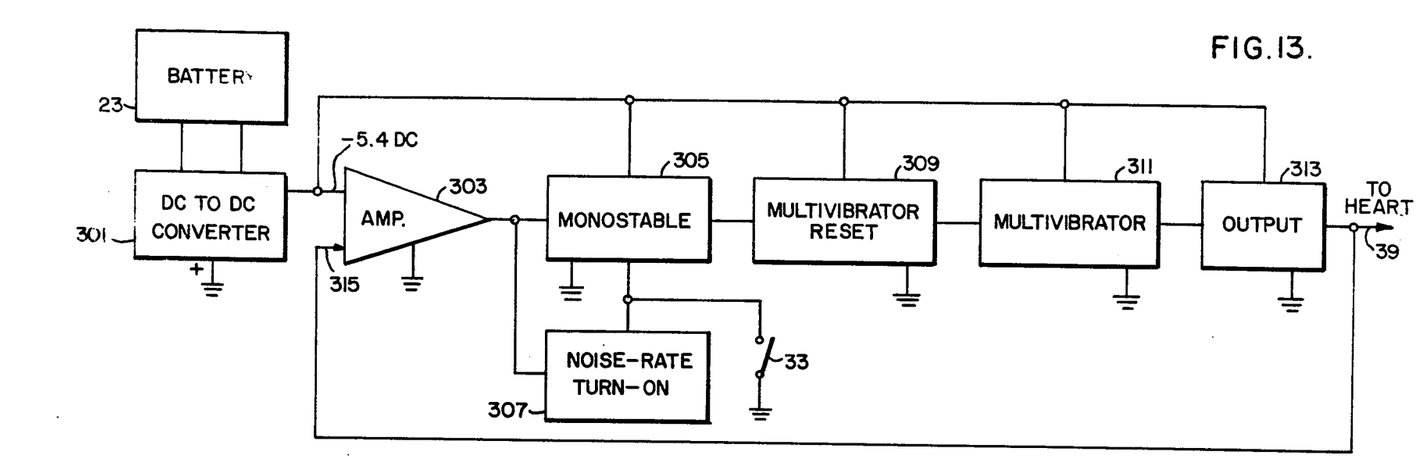
FIG. 13 is a block diagram of a typical electrical circuit of a heart pacer in accordance with this invention.

The output of the battery 23 is about 0.6 volts open circuit; the DC-DC converter 301 derives about −5.4 volts from this output for operating the remainder of the circuit.

The amplifier 303 amplifies any input signal impressed on its input terminal 315 which is greater than 1.5 millivolts to 2.0 millivolts. This stage amplifies R-waves from the heart, pacer pulses and any noise which might be present at the input 315. The gain of this amplifier 303 falls off rapidly once the frequency of the incoming noise is out of the amplifier's band pass.

The monostable 305 performs two different functions. First, when it is triggered by a signal from the amplifier 303, it puts out typically a 0.275 second duration square pulse; and the monostable cannot be triggered on again until it times out. This pulsing interval serves as the pacer's refractory period. The pacer's mode cannot be affected during this time. The amplifier 303 remains sensitive, but the multivibrator 311 cannot be reset until the monostable 305 completes its pulse of 0.275 second. The amplifier 301 remains operative to drive the noise rate turn-on 307. Second, the leading edge of the monostable pulse resets the multivibrator 311.

The multivibrator 311 controls the rate and width of the output pulses of the pacer 21. The multivibrator 311 can operate in two different modes. One mode is the normal rate which is 70±2 beats per minute. The other is the noise rate which is 85±5 beats per minute. In both modes the pulse duration remains at 1.1±.1 milliseconds.

The output 313 is the stage which produces the negative pulse which actually paces the heart.

The multivibrator reset 309 stops the multivibrator 311 from putting out a pulse (heart pacing pulse). If a monostable pulse (duration 0.275) occurs because of an R-wave fed back from the heart or a pacer pulse, this stage 309 resets the multivibrator rate capacitor (not shown) to near zero volts. Every time the multivibrator 311 is reset it waits for 850 milliseconds (70.6 beats per minute) before it puts out another pacer pulse. Every time the pacer 21 itself puts out a heart pacing pulse it resets itself.

The noise-rate turn-on 307 constantly monitors the output of the amplifier 303. If the noise rate circuit senses that the amplifier's output pulses are at a specific frequency (15 hertz ±5 hertz, the noise turn-on frequency) it disables the monostable stage 305. This in turn prevents the multivibrator reset stage 309 from discharging the rate capacitor (not shown) in the multivibrator 311. If the rate capacitor in the multivibrator is not discharged, which happens every time the monostable stage 305 puts out its 0.275 second pulse, the multivibrator 311 continues to run, but the capacitor does not discharge to zero on every pulse and the rate increases to 85±5 beats per minute (the noise rate). When the magnetic reed switch 33 is closed by a magnet, external of the body, the pacer 21 becomes a fixed rate unit at the noise rate.

In the heart pacer under the control of the conduit shown in FIG. 13 (R-waves), when they occur, disable the multivibrator 311 from delivering heart-pacer pulses to the heart. Pulses are only delivered in the absence of R waves. The operation of such a heart pacer is referred to as an R-wave inhibited demand pacer. Typical parameters of the heart pacer in accordance with this invention are:

1. Pulse Duration — 1.1 milliseconds, nominal — 1.0–1.2 milliseconds, range. A sufficiently long pulse duration to always insure heart capture is provided. A minimum pulse duration is desired to conserve electrical power output. If the pulse duration were reduced substantially below the 1.1 milliseconds, the amplitude requirement may become excessive, thereby causing fibrillation.
2. Pulse Amplitude — 8 milliamps, nominal — 7.5 to 8.5 milliamps, range. This amplitude is selected to always provide effective capture after the rise of threshold levels after electrode endothelialization. A higher amplitude, possibly 10 milliamps, may be considered, since a nuclear powered system is not battery energy sensitive, but the possibility of fibrillation might arise with such high levels. A lower amplitude in some rare cases could prevent heart capture.
3. Basic Rate — 70 beats per minute, nominal — 68 to 72 beats per minute range. This rate appears to be the most common required by patients.
4. Noise rate — 85 beats per minute, nominal — 80 to 100 beats per minute, range. This is the rate at which the pacemaker operates when noise interference is so great that it masks the normal Q-R-S heart complex. A rate higher than the basic rate is selected to minimize the possibility of competition with the normal heart rate should it be in normal rhythm.
5. Noise Rate Turn-On — Approximately 20 Hertz. This rate is selected to prevent interference from all conceivable noise modes, microwave ovens and the like, with the exception of a sporadic impulse which would not be fatal. It is sufficiently low to rule out 60 Hertz rates which are the most probable, particularly with the expanding use of microwave ovens.
6. Magnetic Switch Rate — 85 beats per minute, nominal — 80 to 100 beats minute, range. This rate is a fixed rate, at which the pacer operates when energized by a magnet placed near the patient's magnetic reed switch. This turn-on feature allows checking of the pacemaker performance since in the R-wave inhibited mode with normal Q-R-S complexes, the physician cannot tell whether the pacemaker is operating.
7. R-Wave Sensitivity — ±1.75 millivolts, nominal — 1.5 to 2.0 millivolts, range. This sensitivity is selected to assure sensing of the R-wave, and is sufficiently high to prevent interference from abnormal P waves.
8. Refractory Period — 275 milliseconds, nominal — 250 to 300 milliseconds, range. This electronic refractory period begins with either a normal R-wave or the pacemaker stimulus. It is sufficiently long to prevent stimuli during the T-wave onset or decay—this period being the critical period for possible pacemaker induced fibrillation, i.e., no stimulus occurs during the T-wave of normal heart repolarization.

While a preferred embodiment of this invention has been disclosed herein, many modifications thereof are feasible. This invention is not to be restricted except insofar as is necessitated by the spirit of the prior art.

I claim:

1. An electrical generator including a container, a heat source and a thermoelectric unit of the solid-state type having a hot-junction and a cold-junction within said container, means within said container, contacting substantially the whole outer surface of said unit, for applying stress of the hydrostatic type to said unit, and means connecting said hot-junction in heat-deriving relationship with said source.

2. The generator of claim 1 wherein the connecting means includes a portion of the stress-applying means, heat from the source flowing through said portion to the hot-junction, said portion of the stress-applying means being of a material of high thermal conductivity.

3. The generator of claim 1 including means connected to the stress-applying means for applying precompression of the hydrostatic type to the thermoelectric unit.

4. A thermoelectric converter including a container, a thermoelectric unit within said container, a medium within said container, contacting substantially the whole outer surface of said unit, for impressing stress of the hydrostatic type on said unit.

5. The converter of claim 4 wherein the thermoelectric unit is in the form of an elongated member having a hot-junction at one end and a cold-junction at the opposite end, substantially only the portion of the medium contacting said ends being of thermally conducting material and the remainder of the medium being of thermally insulating material.

6. The converter of claim 4 wherein the thermoelectric unit is of the solid-state type.

7. The generator of claim 3 including means, responsive to the precompression applying means, for measuring the magnitude of the precompression.

8. The generator of claim 1 including an outer container and an inner container, the source, unit and stress-applying means being enclosed in said inner container, said outer container including therein means, external to the inner container, and connected to the unit, for deriving electrical pulsations from the output of said unit, and embedding means, within said outer container, for applying pressure of the hydrostatic type to said inner container, and to said deriving means.

9. A radioactive thermoelectric generator including a container, a fuel capsule containing radioactive material constituting a primary source of energy for said generator, a thermoelectric unit of the solid-state type in the form of an elongated member having hot and cold junctions at its ends within said container, a medium within said container contacting substantially the whole outer surface of said member for impressing stress hydrostatically on said member, said stress-impressing medium having at the ends of said member a first thermally conducting portion engaging the hot-junction of said unit and a second thermally-conducting portion engaging the cold-junction of said unit, and the remainder of said stress-impressing medium being thermally insulating, means, including said first portion, connecting said capsule in heat-transfer relationship with said hot-junction, a heat-sink, and means, including said second portion, connecting said heat-sink in heat-deriving relationship with said cold-junction.

10. The generator of claim 9 including means connected to the second portion for compressing said second portion to impress hydrostatic precompression on the member.

11. The generator of claim 10 including means, connected to the stress-impressing medium, for measuring the magnitude of the compression.

12. The generator of claim 11 wherein the measuring means is at least one split ring encircling the second portion, the gap produced in said ring as the second portion is deformed under compressing measuring the magnitude of the compression.

13. The generator of claim 8 wherein the embedding means includes thermally conducting embedding means interposed only between the cold-junction of the thermoelectric unit and the outer container.

14. An electrical generator including a heat source, a thermoelectric unit having a hot-junction and a cold-junction and a container for said unit, said unit being mounted in said container with its hot-junction near one end of said container and its cold-junction near the other end of said container, said source engaging said one end of said container in heat-transfer relationship with said hot-junction, said unit being potted in said container by pressurized potting material which fills said container and supports said container against buckling by said source.

15. The generator of claim 14 wherein the source is enclosed in a cylindrical heat shield encircling said source, said heat shield also serving to support said source against radial displacement.

16. An electrical generator including a heat source, a thermoelectric unit having a hot-junction and a cold-junction, and a container for said unit, said unit being mounted in said container with its hot-junction near one end of said container and its cold-junction near the other end of said container, said source being mounted on said container near said one end, and a cylindrical heat shield having its axis generally along the direction between the said ends of said container, encircling only said source with its inner surface in firm engagement with said source, said shield in addition to providing shield serving to support said source against displacement laterally oof said direction between said ends of said container.

17. An electrical generator including a thermoelectric unit having a hot-junction and a cold-junction, a primary heat source of radioactive material, a first capsule of an alloy predominately of tantalum enclosing said radioactive material, a second capsule of an alloy of platinum and rhodium enclosing said first capsule, a third closed capsule of tantalum enclosing said second capsule, and means connecting said hot-junction in heat-deriving relationship with said third capsule.

18. The converter of claim 4 wherein the thermoelectric unit has a hot-junction in one region thereof and a cold-junction in another region thereof, substantially only the portion of the medium encompassing said one region and the portion of the medium encompassing said other region being of thermally-conducting material, and the remainder of the medium being of thermally insulating material.

19. A radioactive thermoelectric generator including a container, a fuel capsule containing radioactive material constituting a primary source of energy for said generator, a thermoelectric unit of the solid-state type having hot and cold junctions within said container, a medium, within said container, contacting substantially the whole outer surface of said unit for impressing stress hydrostatically on said unit, said medium having at said hot and cold junctions, a first thermally conducting portion engaging the hot-junction of said unit and a second thermally-conducting portion engaging the cold-junction of said unit, and the remainder of said medium being thermally insulating, means, including said first portion, connecting said capsule in heat-transfer relationship with said hot-junction, a heat-sink, and means, including said second portion, connecting said heat-sink in heat-deriving relationship with said cold-junction.

20. A primary source of an electrical generator including a radioactive material, a first capsule of an alloy predominately of tantalum enclosing said material, a second capsule of platinum rhodium enclosing said first capsule and a third closed capsule of tantalum enclosing said second capsule.

21. The source of claim 20 wherein the first capsule has the following composition:
Tungsten 9.6 to 10.2 percent
Hafnium 2.2 to 2.8 percent
Carbon .008 to .0175 percent
Tantalum Remainder
and the second capsule is composed of 10% platinum and the remainder rhodium.

22. The generator of claim 16 including an outer container wherein the source and the container containing the thermoelectric unit are mounted, the heat shield being interposed between said outer container and said source and engaging said outer container.

* * * * *